(12) United States Patent
Bradley et al.

(10) Patent No.: US 8,547,555 B1
(45) Date of Patent: Oct. 1, 2013

(54) SPECTROMETER WITH BUILT-IN ATR AND ACCESSORY COMPARTMENT

(75) Inventors: Michael S. Bradley, Edgerton, WI (US); Federico Izzia, Middleton, WI (US); John M. Coffin, Blue Mounds, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 12 days.

(21) Appl. No.: 13/458,000

(22) Filed: Apr. 27, 2012

(51) Int. Cl.
*G01N 21/55* (2006.01)

(52) U.S. Cl.
USPC ........................................................ 356/445

(58) Field of Classification Search
USPC ........................................................ 356/445
See application file for complete search history.

(56) References Cited

U.S. PATENT DOCUMENTS

| | | | |
|---|---|---|---|
| 5,338,935 A | 8/1994 | Truett et al. | |
| 5,859,434 A | 1/1999 | Messerschmidt | |
| 6,038,022 A | 3/2000 | Jones et al. | |
| 6,414,311 B1 | 7/2002 | Wood et al. | |
| 7,075,645 B2 * | 7/2006 | Gehrlein et al. | 356/328 |
| 7,582,869 B2 | 9/2009 | Sting et al. | |
| 7,652,765 B1 * | 1/2010 | Geshwind et al. | 356/330 |
| 2011/0228279 A1 * | 9/2011 | Lucey | 356/454 |

* cited by examiner

*Primary Examiner* — Tu Nguyen
(74) *Attorney, Agent, or Firm* — Michael C. Staggs

(57) ABSTRACT

The present application is directed to a novel spectrometer configured with a built-in attenuated total reflectance (ATR) and accessory compartment. In particular, an arranged sample analysis compartment provided by the spectrometer performs attenuated total reflectance analysis of a sample and includes a crystal, a tip configured to press the sample against the crystal, and a detector configured to detect light after reflection within the crystal. As part of the configuration, an actuator moves an optical element between a first position wherein the optical element receives modulated light and reflects the modulated light toward the crystal and a second position wherein the optical element does not receive the modulated light so as to instead allow an additionally configured optical component to receive the modulated light.

20 Claims, 16 Drawing Sheets

SPECTROMETER WITH BUILT-IN ATR AND ACCESSORY COMPARTMENT

BACKGROUND

Fourier transform infrared (FTIR) spectrometers are utilized to perform accurate and efficient identification of the chemical composition of a sample. Such spectrometers typically incorporate an interferometer such as a Michelson interferometer that has a beamsplitter and a moving mirror. The interferometer modulates the beam from a source to provide an output beam in which the intensity of the radiation at various wavelengths is varied. The light may be in the near ultraviolet (UV), visible (Vis), near-infrared (NIR), mid-infrared (MIR), and/or far-infrared (FIR) wavelength ranges, and thus, is not limited to the infrared spectral region. The output beam is focused and passed through or reflected from a sample, after which the beam is collected and focused onto a detector. The detector provides a time varying output signal which contains information concerning the wavelengths of absorbance or reflectance of the sample. For example, the intensity of the output light at the one or more wavelengths is compared to the intensity of the input light at the one or more wavelengths to determine characteristics of the sample, such as the absorbance, the transmittance, the fluorescence, the reflectance, etc. Fourier analysis is performed on the output signal data to yield the measured characteristics that provide information about the identity of the components within the sample, their relative concentrations, and possibly other features of the sample.

Conventional FTIR spectrometers include a sample chamber in which a sample is held in a position to be exposed to the light from the interferometer. The sample may take various physical states, i.e., a liquid, a solid, or a gas, and solid samples may have various physical characteristics. For example, a solid material to be analyzed may be in the form of a block or sheet of material (e.g., polymer plastics), in the form of powders or granulates, or in specific formed shapes (e.g., pharmaceutical tablets, pills and capsules).

Multifunctional FTIR spectrometers perform transmission or reflection measurements, or both, on a variety of samples, including liquids and powders as well as shaped solid samples such as pharmaceutical pills and tablets. The various samples can be tested utilizing the same spectrometer system without modification of the spectrometer and without the addition or rearrangement of sample compartments and sample holders. The spectrometer includes a plurality of sample holders configured within a transmission or reflection measurement system.

Attenuated total reflectance (ATR) is a sampling technique used in conjunction with infrared spectroscopy that enables samples to be examined directly in the solid, liquid, or gas state without further preparation. ATR uses a property of total internal reflection resulting in an evanescent wave. Light is passed through a crystal in such a way that it reflects at least once off the internal surface in contact with the sample. This reflection forms the evanescent wave which extends into the sample. The penetration depth into the sample is determined by the wavelength of light, the angle of incidence, and the indices of refraction for the crystal and the medium being probed. The number of reflections may be varied by varying the angle of incidence. The beam is collected by a detector as it exits the crystal. Example materials for ATR crystals include germanium, zinc selenide, and diamond.

SUMMARY

In an illustrative embodiment, a spectrometer for analyzing a sample is provided. The spectrometer includes, but is not limited to, a base plate, a light source, an interferometer, an accessory compartment, a sample analysis device, a first optical element, a second optical element, and an actuator. The light source is mounted to the base plate and configured to transmit light. The interferometer is mounted to the base plate to receive light from the light source and to form modulated light. The accessory compartment is configured to accept a sample analysis accessory device and includes a first wall, a second wall, and a third wall extending from the base plate. The third wall extends between the first wall and the second wall. The first wall includes a first light port configured to accept first light. The sample analysis device is mounted to the base plate and separated from the accessory compartment by the first wall. The sample analysis device is configured to perform attenuated total reflectance analysis of a sample and includes a crystal configured to receive second light, a tip configured to press the sample against the crystal, and a detector configured to detect third light after reflection of the second light within the crystal. The first optical element is mounted to the base plate and is configured to receive and to reflect the modulated light toward the first light port to form the first light. The second optical element is mounted to the base plate. The actuator is mounted to the second optical element and is configured to move the second optical element between a first position and a second position. In the first position, the second optical element is configured to receive the modulated light and to reflect the modulated light toward the crystal to form the second light such that the first optical element does not receive the modulated light. In the second position, the second optical element does not receive the modulated light thereby unblocking the first optical element from receiving the modulated light.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

As understood by a person of skill in the art, Fourier transform infrared (FTIR) spectroscopy is a measurement technique where, instead of recording the amount of energy absorbed in each individual spectral range, the energy across the entire spectra is collected by a single detector. The light source emits broadband infrared energy that is directed into an interferometer, such as a Michelson interferometer, which splits the light. The light that comes out of the interferometer is directed into a sample compartment of a sample analysis device. The light interacts with the sample and is either transmitted through or reflected off of the surface of the sample depending on the type of analysis performed by the sample analysis device. After exiting the sample compartment, the light reaches a detector and is measured to produce a sample analysis signal. Using the Fourier transform, the sample analysis signal is transformed from the frequency domain to the time domain to obtain spectral information about the sample. Typically, the FTIR spectrometer includes a laser for internal calibration of the interferometer.

Figure 1:
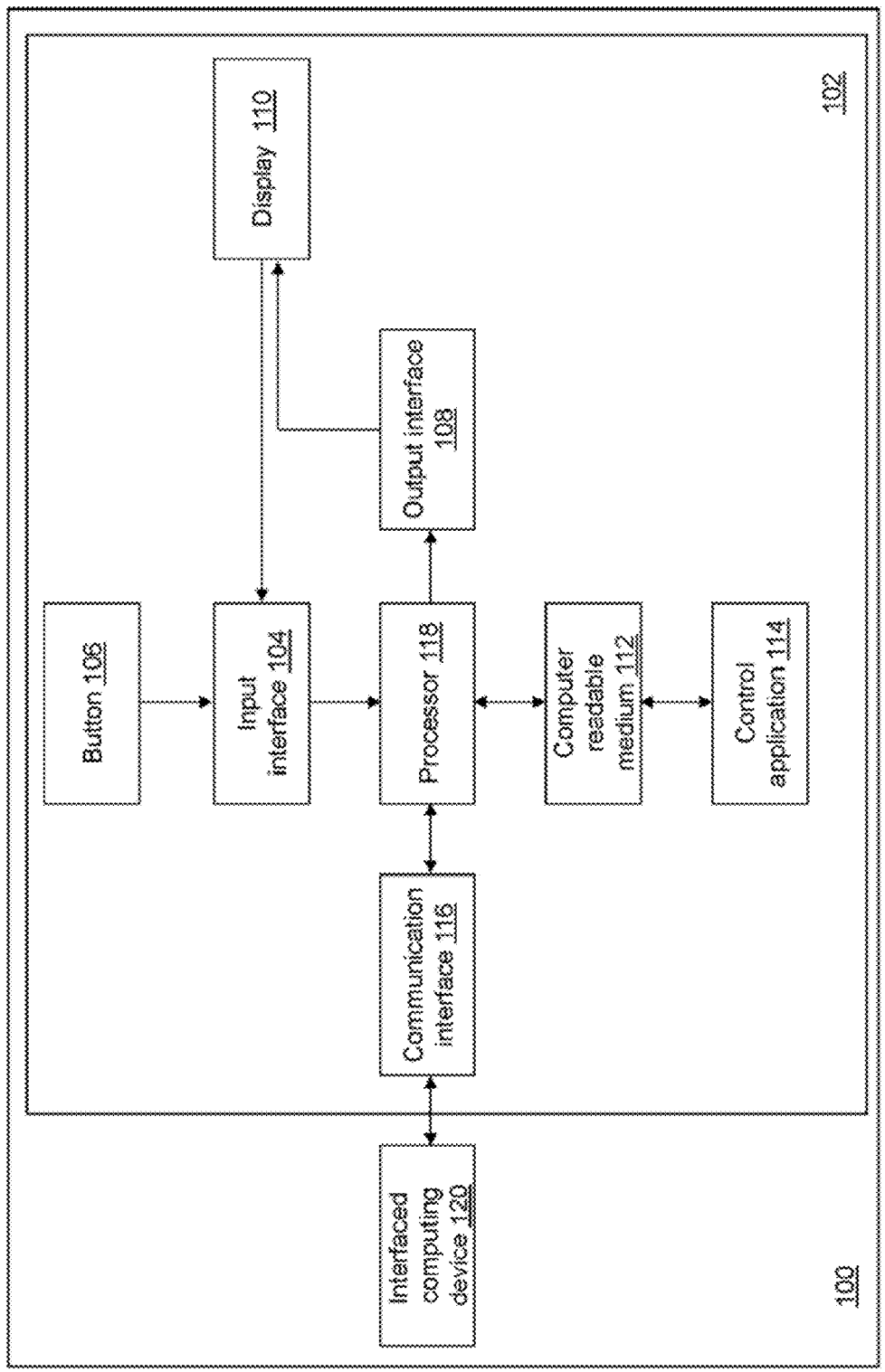
FIG. 1 depicts a block diagram of a spectroscopy system in accordance with an illustrative embodiment.

With reference to FIG. 1, a block diagram of a spectrometry system 100 is shown in accordance with an illustrative embodiment. In the illustrative embodiment, spectrometry system 100 may include a spectrometer 102 and an interfaced computing device 120 to which spectrometer 102 may be connected. Spectrometer 102 need not connect to interfaced computing device 120. If connected, spectrometer 102 and interfaced computing device 120 may be connected directly or through a network. The network may be any type of wired and/or wireless public or private network including a cellular network, a local area network, a wide area network such as the Internet, etc. Spectrometer 102 may send and receive information to/from interfaced computing device 120. For example, spectrometer 102 may send results obtained for a sample for storage on interfaced computing device 120. As another example, spectrometer 102 may receive software updates from interfaced computing device 120 and/or receive commands from interfaced computing device 120. The commands may control operation of one or more components of spectrometer 102. Interfaced computing device 120 may include a computing device of any form factor such as a personal digital assistant, a desktop computer, a laptop computer, an integrated messaging device, a cellular telephone, a smart phone, a pager, etc. without limitation.

Spectrometer 102 may include an input interface 104, a button 106, an output interface 108, a display 110, a computer-readable medium 112, a control application 114, a communication interface 116, and a processor 118. Different and additional components may be incorporated into spectrometer 102. Input interface 104 provides an interface for receiving information from the user for entry into spectrometer 102 as known to those skilled in the art. Input interface 104 may use various input technologies including, but not limited to, a keyboard, a pen and touch screen, a mouse, a track ball, a touch screen, a keypad, one or more buttons including button 106, etc. to allow the user to enter information into spectrometer 102 or to make selections presented in a user interface displayed on display 110. Spectrometer 102 may have one or more input interfaces that use the same or a different input interface technology.

Output interface 108 provides an interface for outputting information for review by a user of spectrometer 102. For example, output interface 108 may include an interface to display 110, a speaker, a printer, etc. Display 110 may be a thin film transistor display, a light emitting diode display, a liquid crystal display, or any of a variety of different displays known to those skilled in the art. Spectrometer 102 may have one or more output interfaces that use the same or a different interface technology. The same interface may support both input interface 104 and output interface 108. For example, a touch screen both allows user input and presents output to the user. Display 110, the speaker, and/or the printer further may be accessible to spectrometer 102 through communication interface 116.

Computer-readable medium 112 is an electronic holding place or storage for information so that the information can be accessed by processor 118 as known to those skilled in the art. Computer-readable medium 112 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., CD, DVD, . . . ), smart cards, flash memory devices, etc. Spectrometer 102 may have one or more computer-readable media that use the same or a different memory media technology. Spectrometer 102 also may have one or more drives that support the loading of a memory media such as a CD or DVD.

Communication interface 116 provides an interface for receiving and transmitting data between devices using various protocols, transmission technologies, and media as known to those skilled in the art. Communication interface 116 may support communication using various transmission media that may be wired or wireless. Spectrometer 102 may have one or more communication interfaces that use the same or a different communication interface technology. Data and messages may be transferred between spectrometer 102 and interfaced computing device 124 using communication interface 116.

Processor 118 executes instructions as known to those skilled in the art. The instructions may be carried out by a special purpose computer, logic circuits, or hardware circuits. Thus, processor 118 may be implemented in hardware, firmware, or any combination of these methods and/or in combination with software. The term "execution" is the process of running an application or the carrying out of the operation called for by an instruction. The instructions may be written using one or more programming language, scripting language, assembly language, etc. Processor 118 executes an instruction, meaning that it performs/controls the operations called for by that instruction. Processor 118 operably couples with output interface 108, with input interface 104, with computer-readable medium 112, and with communication interface 116 to receive, to send, and to process information.

Processor 118 may retrieve a set of instructions from a permanent memory device and copy the instructions in an executable form to a temporary memory device that is generally some form of RAM. Spectrometer 102 may include a plurality of processors that use the same or a different processing technology.

Control application 114 performs operations associated with controlling, maintaining, updating, etc. the operation of spectrometer 102. Some or all of the operations described herein may be controlled by instructions embodied in control application 114. The operations may be implemented using hardware, firmware, software, or any combination of these methods. With reference to the example embodiment of FIG. 1, control application 114 is implemented in software (comprised of computer-readable and/or computer-executable instructions) stored in computer-readable medium 112 and accessible by processor 118 for execution of the instructions that embody the operations of control application 114. Control application 114 may be written using one or more programming languages, assembly languages, scripting languages, etc.

Figure 2:
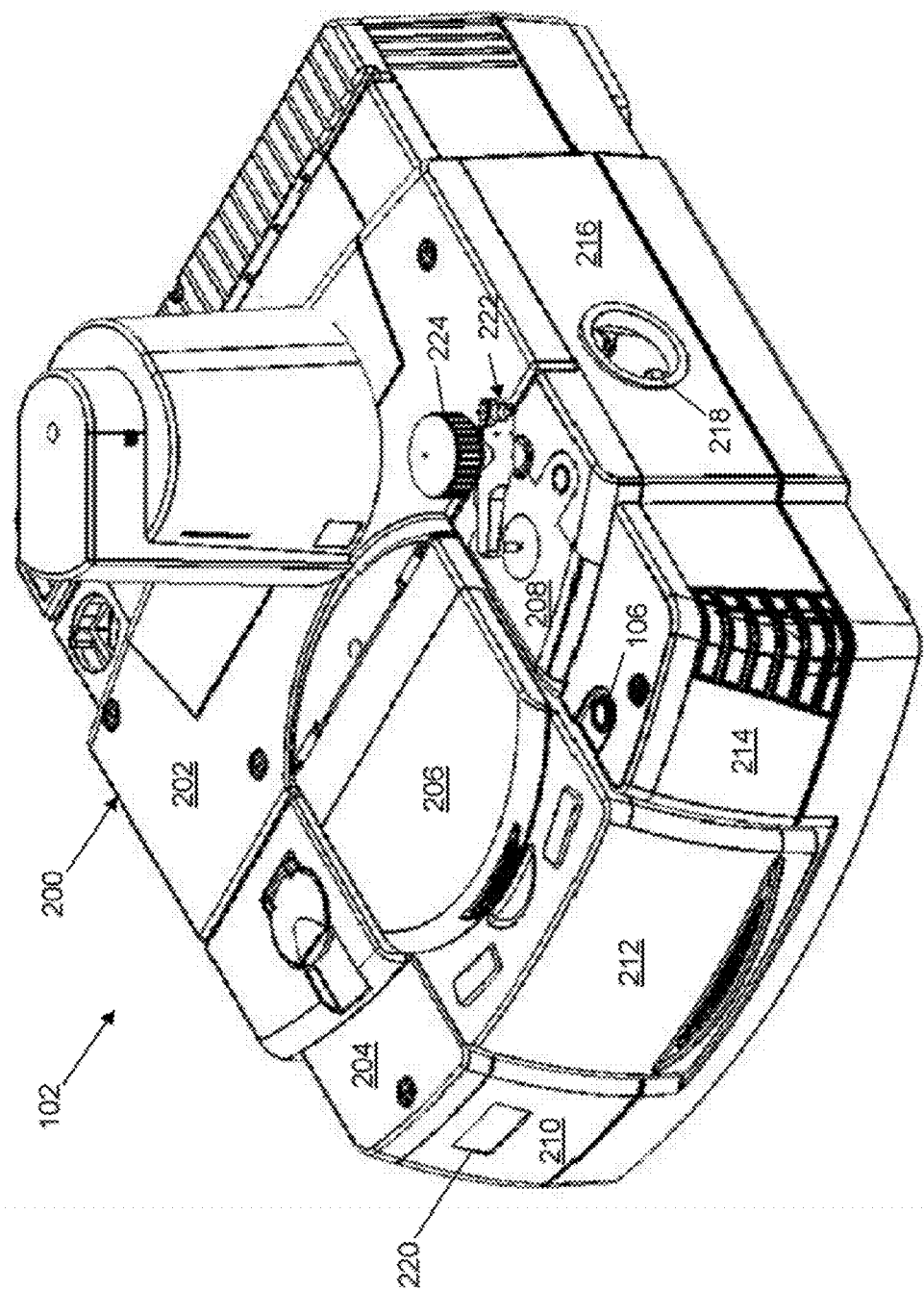
FIG. 2 depicts a perspective view of a spectrometer in accordance with an illustrative embodiment.

With reference to FIG. 2, a perspective view of spectrometer 102 is shown in accordance with an illustrative embodiment. The components of spectrometer 102 are mounted within or to a housing 200 and may be arranged in a variety of manners. As used in this disclosure, the term "mount" includes join, unite, connect, associate, insert, hang, hold, affix, attach, fasten, bind, paste, secure, bolt, screw, rivet, solder, weld, glue, form over, layer, and other like terms. The phrases "mounted on" and "mounted to" include any interior or exterior portion of the element referenced. As used herein, the mounting may be a direct mounting between the referenced components or an indirect mounting through intermediate components between the referenced components.

Housing 200 may include a plurality of walls that surround one or more of the components of spectrometer 102. For example, housing 200 may include a top bench compartment wall 202, a top detector wall 204, a top accessory compartment wall 206, a top ATR compartment wall 208, a front detector wall 210, a front accessory compartment wall 212, a front ATR compartment wall 214, a left side wall 400 (shown with reference to FIG. 4), a right side wall 216, a base plate 500 (shown with reference to FIG. 5), and a back wall 502 (shown with reference to FIG. 5). In an illustrative embodiment, electrical connectors that may embody an interface for input interface 104, output interface 108, and communication interface 116 are mounted in back wall 502. In the illustrative embodiment, button 106 is mounted on top ATR compartment wall 208 and triggers the operation of spectrometer 102 either on or off. Thus, measurements may be initiated by selecting button 106 that triggers initiation of a measurement sequence by one or more components of spectrometer 102 under control of control application 114.

In the illustrative embodiment, a bench compartment is housed generally between top bench compartment wall 202, base plate 500, left side wall 400, right side wall 216, and back wall 502. In the illustrative embodiment, a detector compartment is housed generally between top detector wall 204, base plate 500, left side wall 400, the bench compartment, an accessory compartment 300 (shown with reference to FIG. 3), and front detector wall 210. In the illustrative embodiment, accessory compartment 300 is housed generally between top accessory compartment wall 206, floor plate 302 (shown with reference to FIG. 3), the bench compartment, the detector compartment, an ATR compartment, and front accessory compartment wall 212. In the illustrative embodiment, the ATR compartment is housed generally between top ATR compartment wall 208, base plate 500, the bench compartment, accessory compartment 300, front ATR compartment wall 214, and right side wall 216. Other compartment arrangements are possible. In the illustrative embodiment, right side wall 216 includes a first light port 218, front detector wall 210 includes a detector output port 220, and an ATR arm 222 is mounted to top ATR compartment wall 208 for rotational movement of ATR arm 222 toward and away from top ATR compartment wall 208. ATR arm 222 may include an ATR knob 224.

Figure 3:
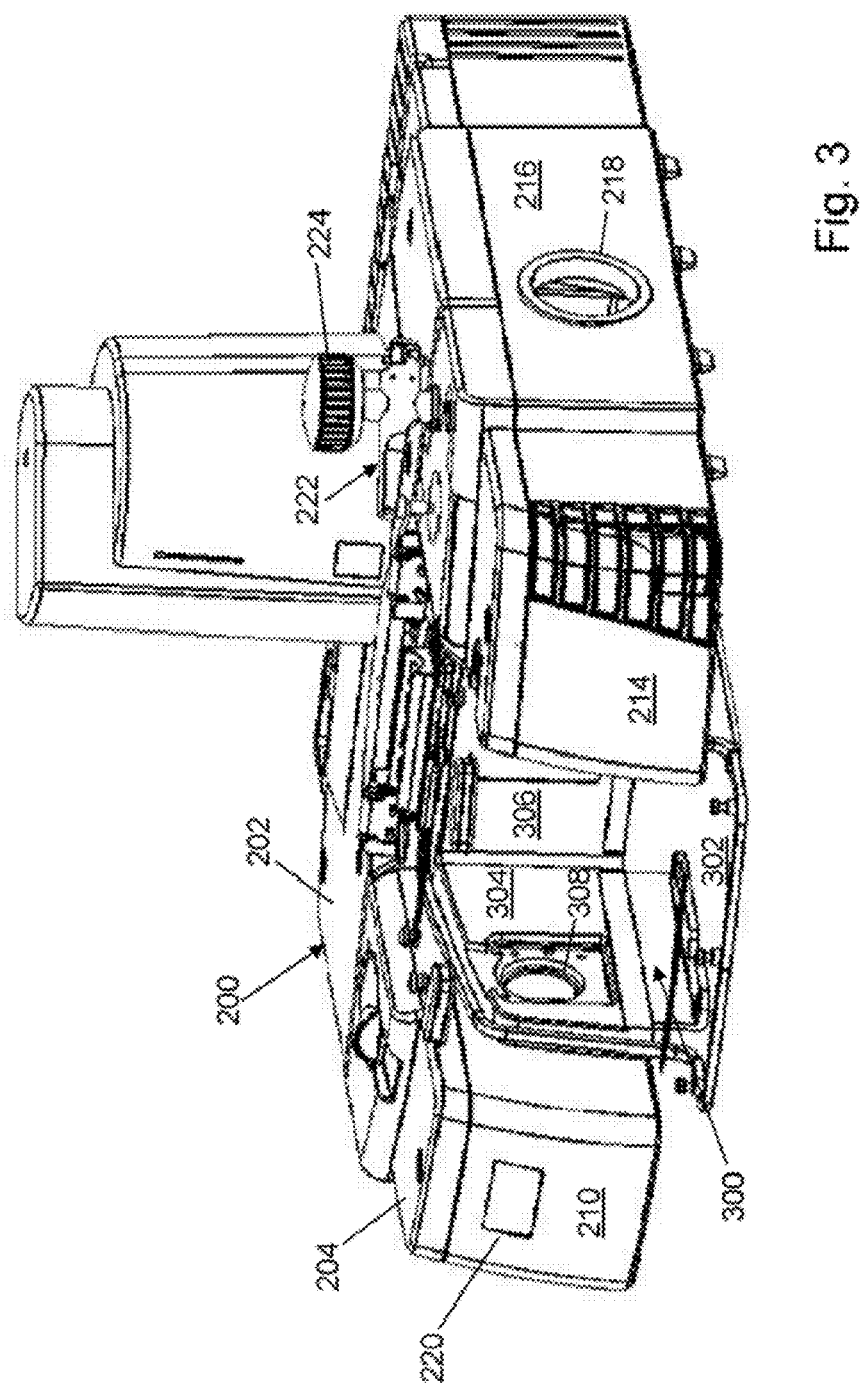
FIG. 3 depicts a right side perspective view of the spectrometer of FIG. 2 without cover plates over an accessory compartment.
Figure 4:
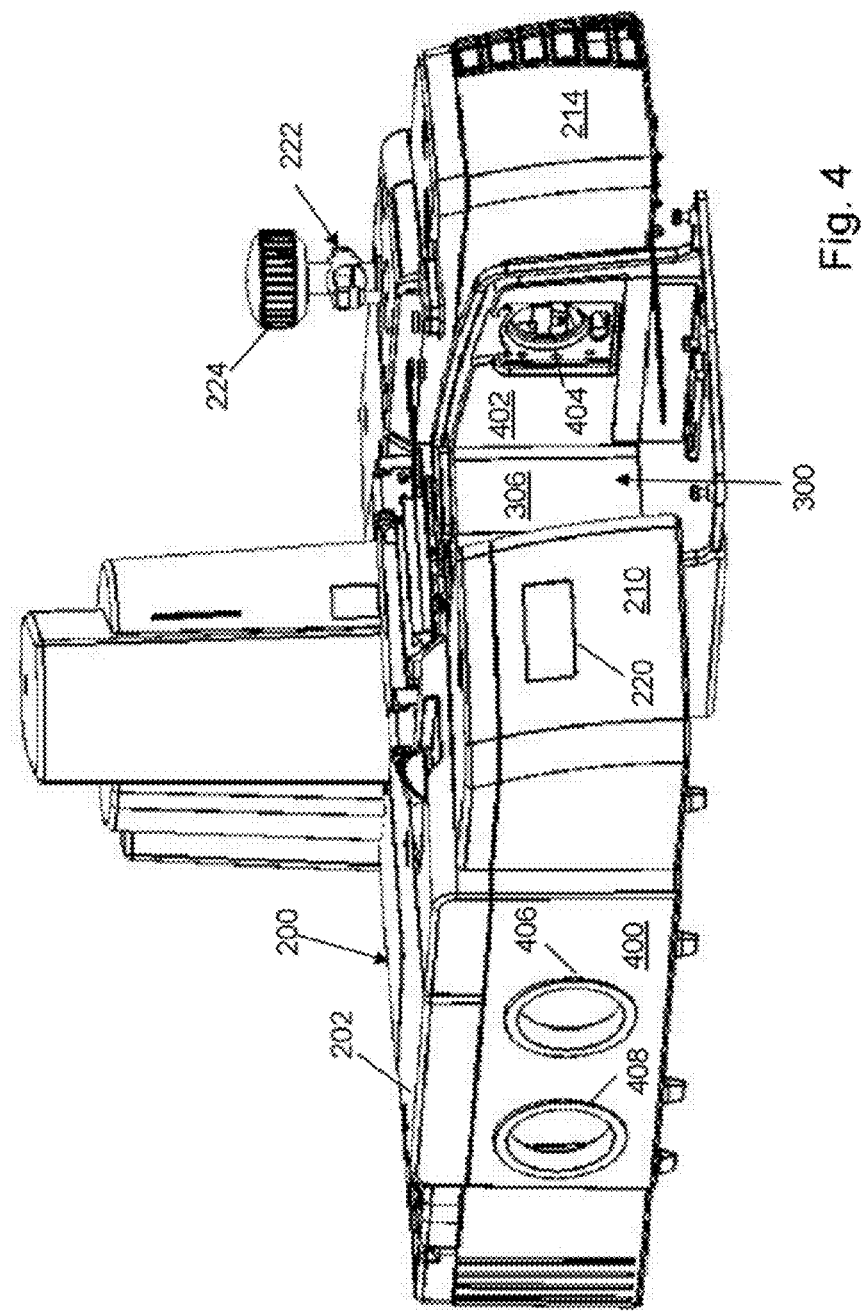
FIG. 4 depicts a left side perspective view of the spectrometer of FIG. 2 without cover plates over an accessory compartment.

With reference to FIG. 3, a right side perspective view of spectrometer 102 is shown in accordance with an illustrative embodiment with top accessory compartment wall 206 and front accessory compartment wall 212 removed to show accessory compartment 300. With reference to FIG. 4, a left side perspective view of spectrometer 102 is shown in accordance with an illustrative embodiment with top accessory compartment wall 206 and front accessory compartment wall 212 removed to show accessory compartment 300. Accessory compartment 300 may be defined by top accessory compartment wall 206, front accessory compartment wall 212, floor plate 302, a left accessory compartment wall 304, a back accessory compartment wall 306, and a right accessory compartment wall 402 (shown with reference to FIG. 4). In the illustrative embodiment, left accessory compartment wall 304 includes a second light port 308 through which light can be provided from accessory compartment 300 to the detector compartment depending on a type of sample analysis accessory device mounted within accessory compartment 300. Though not shown, accessory compartment 300 includes one or more electrical connectors that may provide power to the sample analysis accessory device mounted within accessory compartment 300, may receive signals from the sample analysis accessory device mounted within accessory compartment 300, and/or may send signals to the sample analysis accessory device mounted within accessory compartment 300. The signals may be sent/received by spectrometer 102 and/or by interfaced computing device 124. Illustrative sample analysis accessory devices include a gas chromatography (GC) IR (GC-IR) device, a near IR (NIR) integrating sphere device, a NIR or mid-IR (MIR) fiber optic probe, a thermogravimetric analysis (TGA) device, an IR microscope, an FT-Raman device, a diffuse reflectance device, a single-bounce or multiple-bounce ATR device, a single-bounce or multiple-bounce horizontal ATR (HATR) device, a specular reflectance device, a grazing incidence angle reflectance device, a photoacoustic device, a liquid chromatography device, a photoelastic modulation (PEM) device, etc.

In the illustrative embodiment, right accessory compartment wall 402 includes a third light port 404 through which light can be provided from/to the ATR compartment to/from accessory compartment 300 depending on the type of sample analysis accessory device mounted within accessory compartment 300. In the illustrative embodiment, left side wall 400 includes a fourth light port 406 and a fifth light port 408. A fewer or a greater number of input and output ports may be included in the walls of spectrometer 102. First light port 218, fourth light port 406, and fifth light port 408 receive or transmit light exterior of spectrometer 102 as defined by base plate 500.

Figure 5:
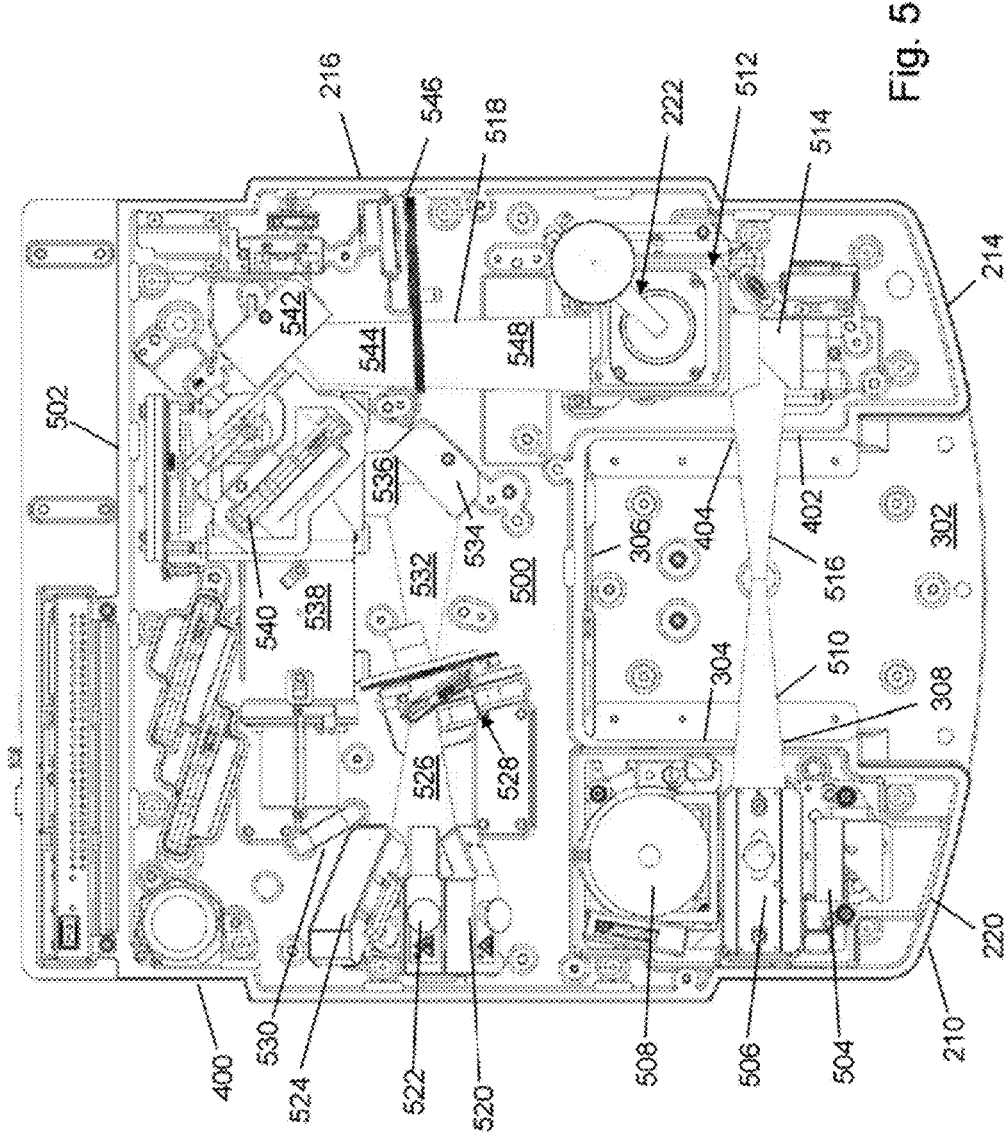
FIG. 5 depicts a top view of the spectrometer of FIG. 2 without any cover plates.

With reference to FIG. 5, a top view of spectrometer 102 is shown in accordance with an illustrative embodiment with front accessory compartment wall 212, top bench compartment wall 202, top detector wall 204, top accessory compartment wall 206, and top ATR compartment wall 208 removed to show an interior of spectrometer 102. In an illustrative embodiment, the detector compartment includes a plurality of detectors and an optical element (not shown) positioned to receive a light beam 510 from accessory compartment 300. For example, in the illustrative embodiment, the detector compartment includes a first detector 504, a second detector 506, and a third detector 508. For illustration, first detector 504 may be a deuterated triglycine sulfate (DTGS) detector, second detector 506 may be a deuterated, L-alanine doped triglycine sulfate (DLaTGS) detector, and third detector 508 may be a nitrogen-cooled mercury-cadmium-telluride (MCT) detector though of course other types of detectors and arrangements of detectors may be used. The optical element may be mounted to an actuator, which moves the optical element to reflect the received light beam 510 to the selected detector. The actuator may be used to control translational and/or rotational movement of the optical element. Illustrative actuators, as used herein, include an electric motor, a servo, stepper, or piezo motor, a pneumatic actuator, a gas motor, etc. The actuator further may move the optical element to reflect the received light beam 510 through detector output port 220 and to an externally mounted detector. In an illustrative embodiment, the optical element is an elliptical mirror.

In an illustrative embodiment, the ATR compartment includes an ATR 512, which includes ATR arm 222 and an optical element 514 positioned to reflect/receive a light beam 516 to/from accessory compartment 300 through third light port 404. Optical element 514 further may be positioned to reflect/receive a light beam 548 to/from the bench compartment.

In an illustrative embodiment, the bench compartment includes a light source that may include a plurality of light sources that emit light at one or more wavelengths selected for analysis of a sample. The light source may emit in the ultraviolet (UV), visible, IR, NIR, FIR, near-UV, etc. Thus, light emitted from the light source may not be visible. In the illustrative embodiment of FIG. 5, the light source includes a first light source 520 and a second light source 522. For illustration, first light source 520 may be an IR source and second light source 522 may be a white light source. In an illustrative embodiment, the bench compartment further includes a Raman detector 524.

An optical element 600 (shown with reference to FIG. 6) may be mounted to an actuator (not shown), which moves optical element 600 to reflect light 526 received from first light source 520 or second light source 522 toward an aperture device 528. The actuator may be used to control translational and/or rotational movement of optical element 600. The actuator further may move optical element 600 to reflect light received from aperture device 528 toward Raman detector 524. In an illustrative embodiment, optical element 600 is an elliptical mirror.

The actuator still further may move optical element 600 to reflect light received from aperture device 528 toward an optical element 530 or to receive light reflected from optical element 530 through fifth light port 408. In an illustrative embodiment, optical element 530 is a parabolic mirror. In an illustrative embodiment, the aperture device 528 automatically sets the correct aperture size depending upon the resolution and spectral range selected for spectrometer 102. Aperture device 528 may include an iris aperture and an iris filter wheel.

Figure 6:
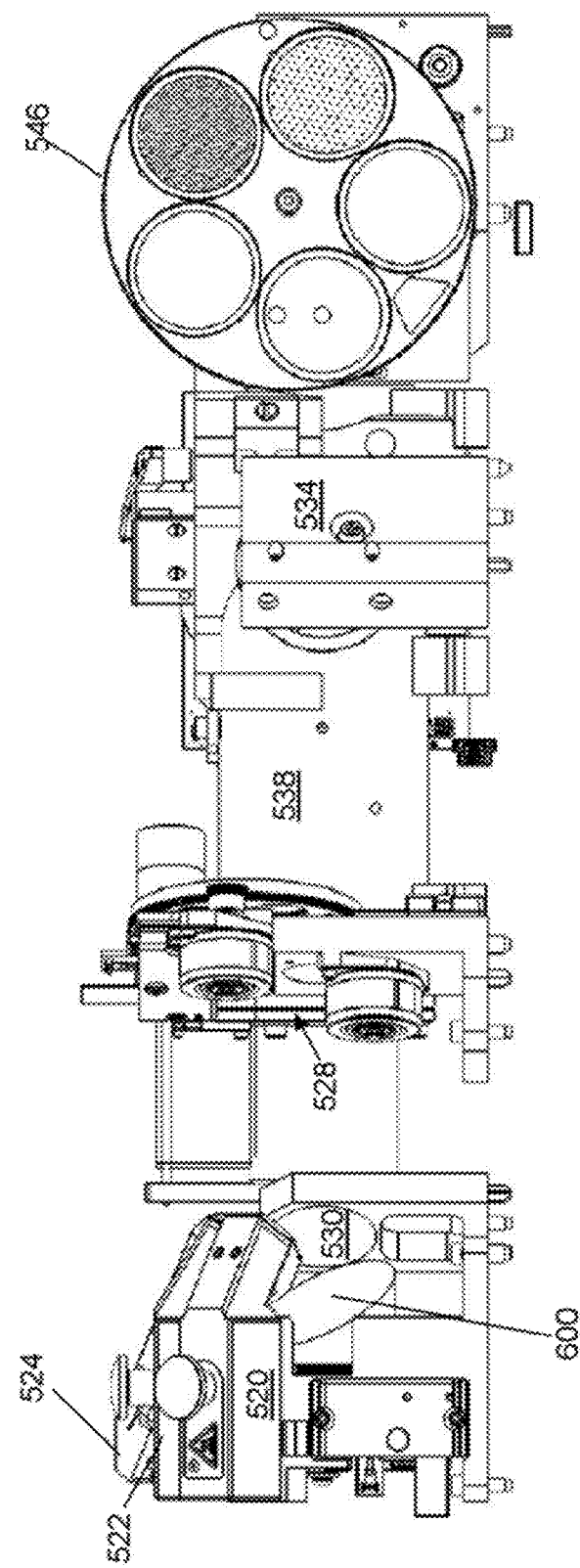
FIG. 6 depicts a side view of a portion of the bench compartment of the spectrometer of FIG. 2 in accordance with an illustrative embodiment.

Aperture device 528 receives/transmits light 532 from/to an optical element 534. In an illustrative embodiment, optical element 534 is a parabolic mirror that reflects light 536 to/from an interferometer 538. Interferometer 538 includes a beamsplitter 540 selected based on the type of sample analysis accessory device selected for operation. Spectrometer 102 further may include an automatic beamsplitter exchanger that automatically changes the beamsplitter inserted in interferometer 538. An optical element 542 receives light from beamsplitter 540 and reflects light 544 toward optical element 514 mounted within the ATR compartment. In an illustrative embodiment, optical element 542 is a flat mirror. Light 544 may pass through a validation wheel 546 to form filtered light 548 before reaching optical element 514. Validation wheel 546 may be configured to test spectrometer 102 using Schott NG-11 and NIST traceable standards as understood by a person of skill in the art. With reference to FIG. 6, a side view of components of the bench compartment of spectrometer 102 is shown in accordance with an illustrative embodiment.

Figure 7:
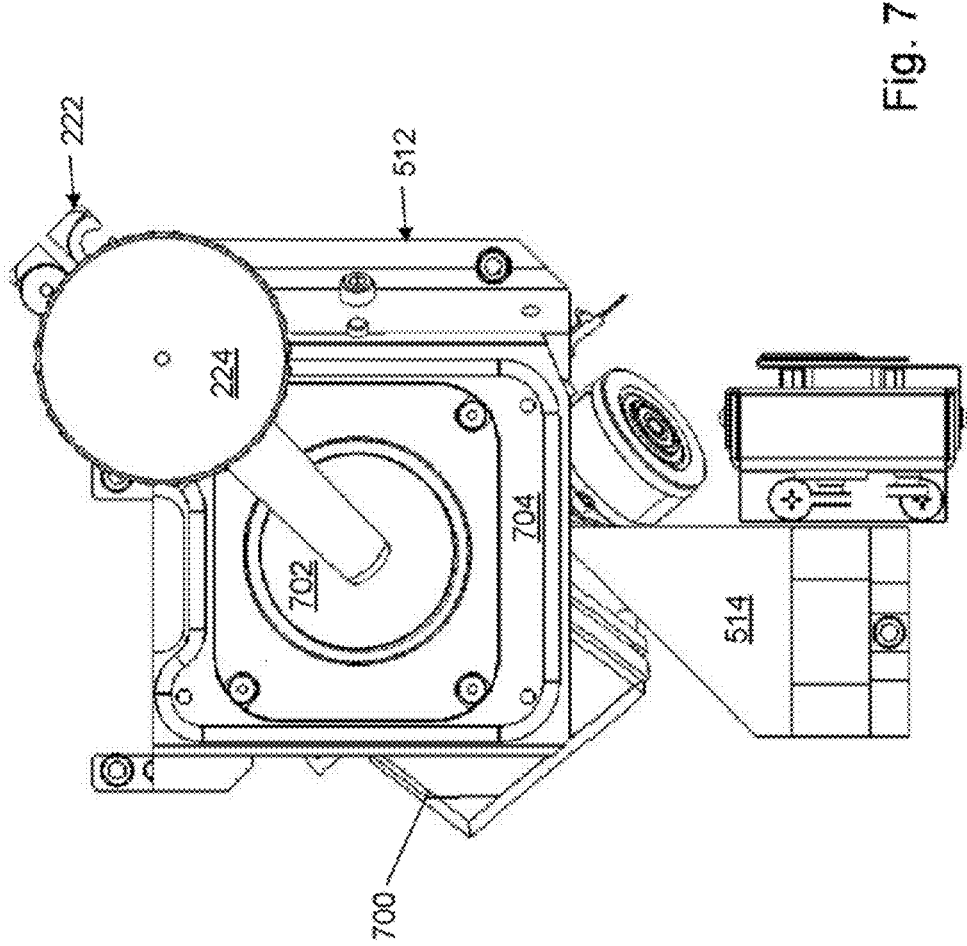
FIG. 7 depicts a top view of an ATR compartment of the spectrometer of FIG. 2 in accordance with an illustrative embodiment.

With reference to FIG. 7, a top view of ATR 512 is shown in accordance with an illustrative embodiment. ATR 512 includes a flipper mirror 700, ATR arm 222, an ATR puck 702, and a platform 704. ATR arm 222 is mounted to base plate 500. ATR puck 702 includes a crystal. For example, in an illustrative embodiment, the crystal is a diamond and ATR puck 702 is a parallel-sided plate. As a result, in the illustrative embodiment, ATR 512 is configured to perform HAIR analysis of a sample. In other embodiments, the crystal may be formed of zinc selenide, germanium, KRS-5, etc. Platform 704 is mounted to ATR arm 222 and positioned generally flush with top ATR compartment wall 208.

Figure 8:
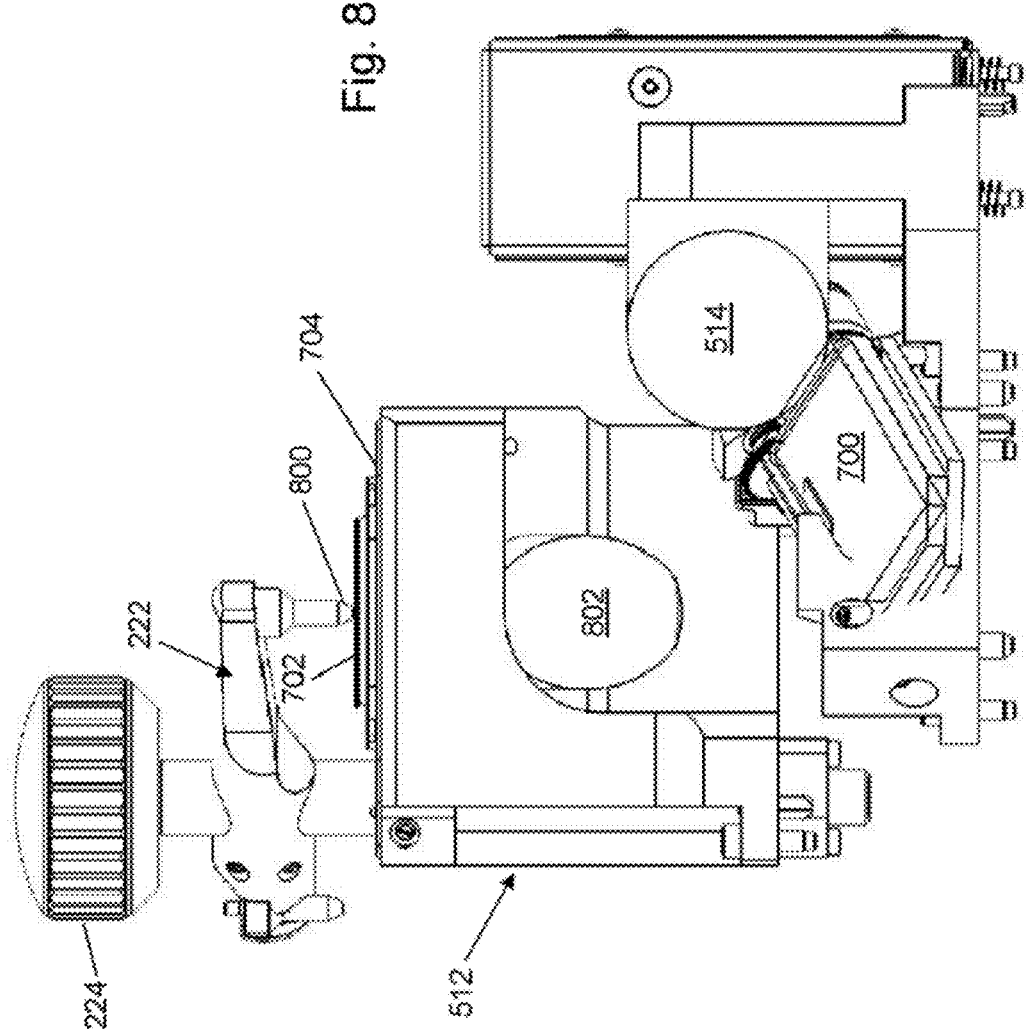
FIG. 8 depicts a left side view of the ATR compartment of FIG. 7 in accordance with an illustrative embodiment.
Figure 9:
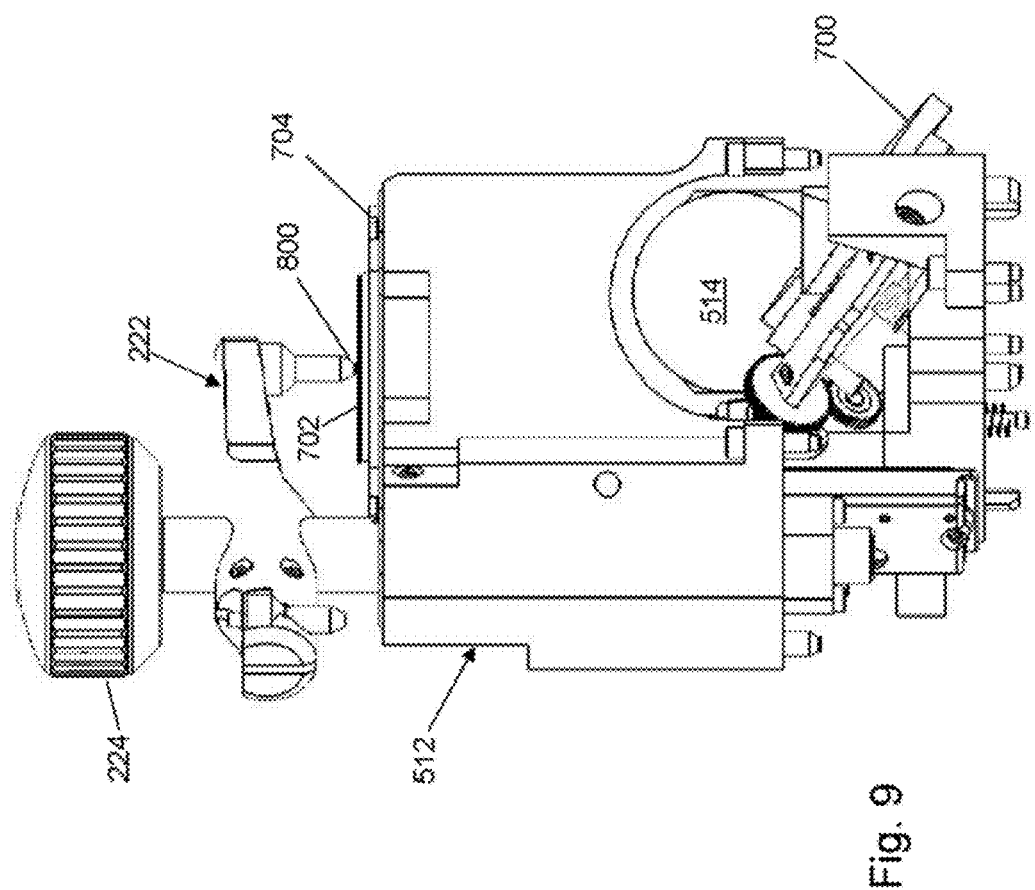
FIG. 9 depicts a back view of the ATR compartment of FIG. 7 with a flipper mirror in a down position in accordance with an illustrative embodiment.
Figure 10:
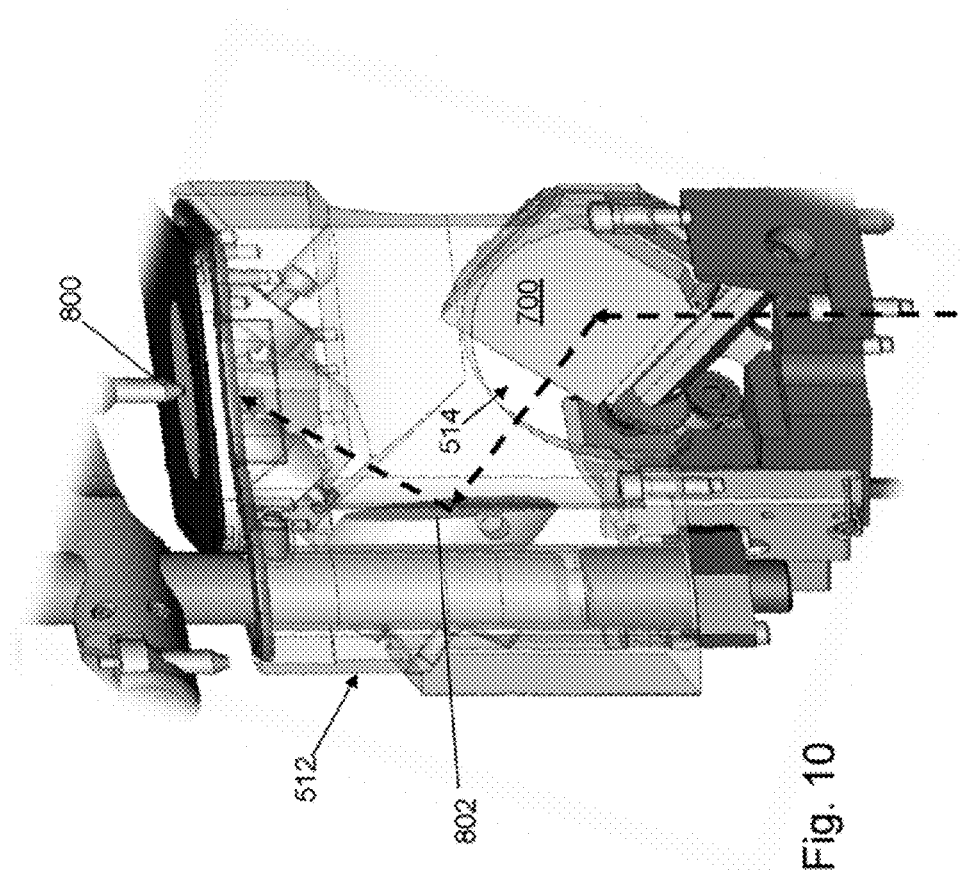
FIG. 10 depicts a back view of the ATR compartment of FIG. 7 with a flipper mirror in an up position in accordance with an illustrative embodiment.

With reference to FIG. 8, a left side view of ATR 512 with flipper mirror 700 down is shown in accordance with an illustrative embodiment. ATR 512 further includes an ATR tip 800 (shown with reference to FIG. 8) extending from ATR arm 222 and an optical element 802. In an illustrative embodiment, optical element 802 is a parabolic mirror. With reference to FIG. 9, a back view of ATR 512 with flipper mirror 700 down is shown in accordance with an illustrative embodiment. With reference to FIG. 10, a back view of ATR 512 with flipper mirror 700 up is shown in accordance with an illustrative embodiment.

Figure 11:
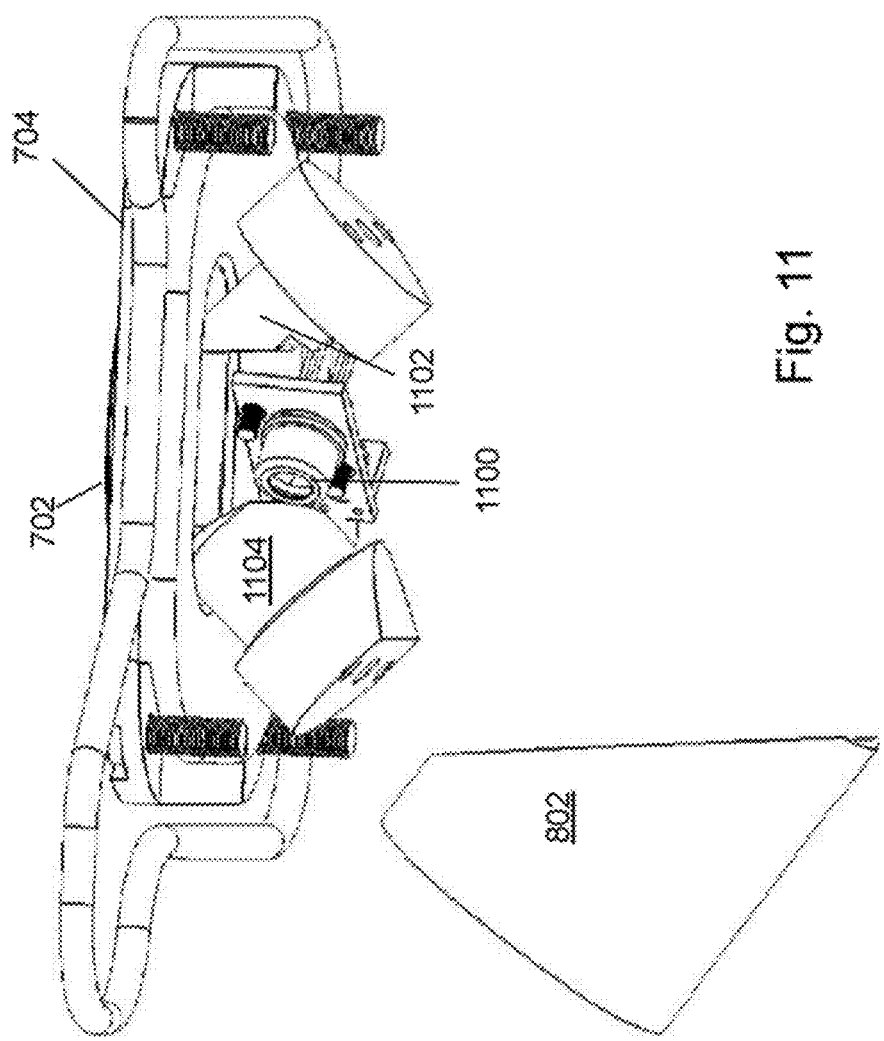
FIG. 11 depicts a back bottom perspective view of components of the ATR compartment of FIG. 7 in accordance with an illustrative embodiment.
Figure 12:
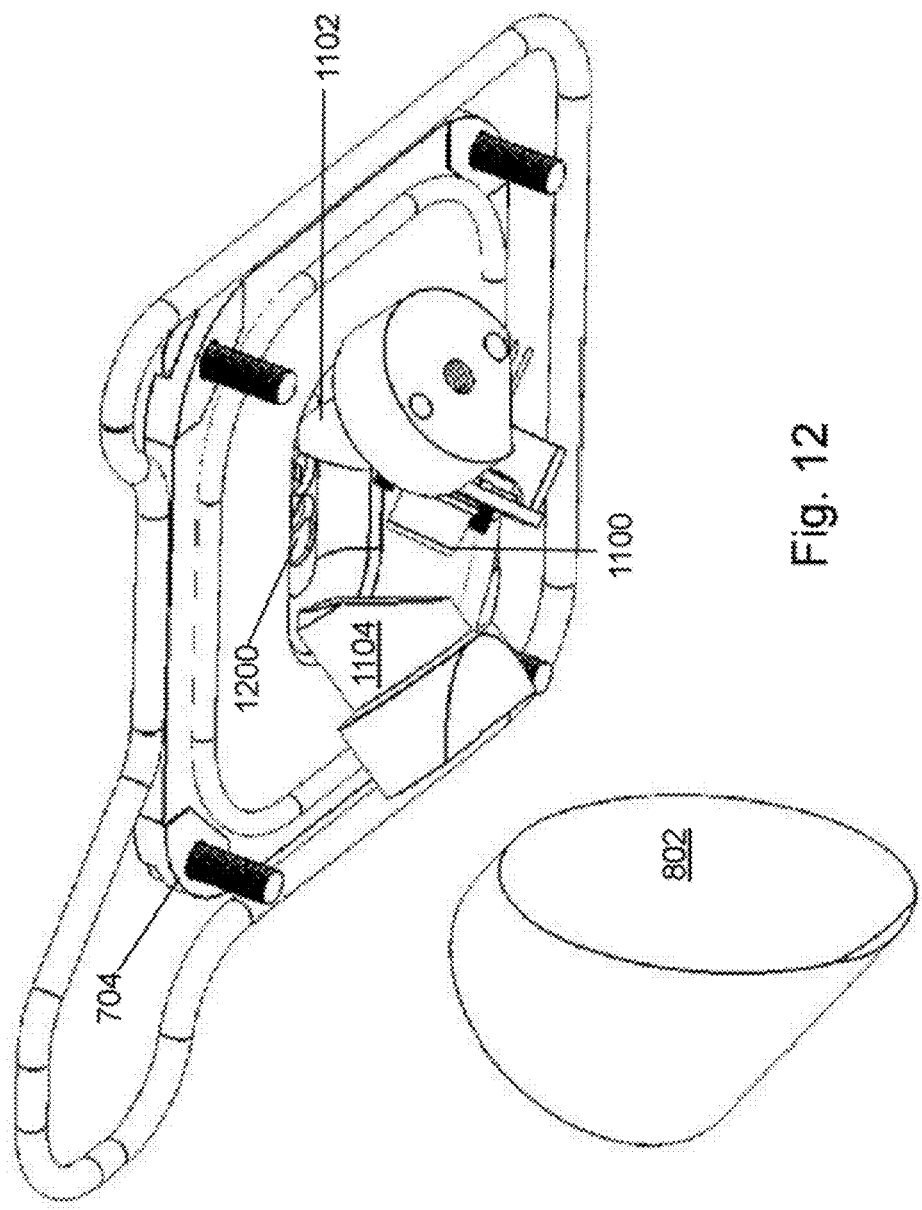
FIG. 12 depicts a left side bottom perspective view of components of the ATR compartment of FIG. 7 in accordance with an illustrative embodiment.

With reference to FIG. 11, a back bottom perspective view of additional components of ATR 512 is shown in accordance with an illustrative embodiment. With reference to FIG. 12, a left side bottom perspective view of the additional components of ATR 512 is shown in accordance with an illustrative embodiment. ATR 512 further includes a first optical element 1102 and a second optical element 1104. In an illustrative embodiment, first optical element 1102 and second optical element 1104 are elliptical mirrors.

To use ATR 512, a user may rotate ATR arm 222 away from ATR puck 702 and place a sample in either liquid or solid form on or in ATR puck 702. For example, the user may use a pipette to place a drop of the sample on ATR puck 702. The user may rotate ATR arm 222 toward ATR puck 702 after placement of the drop on ATR puck 702. The user may then rotate ATR knob 224 to press the sample between ATR tip 800 and an upper surface of ATR puck 702 so that the crystal adequately contacts the sample as understood by a person of skill in the art. One or more of these operations may be automated.

After depression of button 106, filtered light 548 is directed onto flipper mirror 700 positioned in the up position. An actuator is mounted to flipper mirror 700 to lower and raise flipper mirror 700 between a first down position as shown in FIG. 9 and a second up position as shown in FIG. 10. In the first position, flipper mirror 700 does not receive filtered light 548, which is instead received by optical element 514 which reflects filtered light 548 into accessory compartment 300 to form light 516. In the second position, flipper mirror 700 is positioned to receive filtered light 548 and to reflect the received filtered light 548 toward optical element 802 and the crystal such that optical element 514 does not receive filtered light 548 or form light 516.

Optical element 802 receives light reflected from flipper mirror 700 and reflects the received light toward first optical element 1102. First optical element 1102 receives light reflected from optical element 802 and reflects the received light toward a lower surface 1200 (shown with reference to FIG. 12) of ATR puck 702. ATR puck 702 is formed of an optically dense crystal with a high refractive index at a certain angle. This internal reflectance creates an evanescent wave that extends beyond the surface of the crystal and into the sample held in contact with the crystal. This evanescent wave protrudes a few microns beyond the crystal surface and into the sample. In regions of the infrared spectrum where the sample absorbs energy, the evanescent wave is attenuated or altered. The attenuated energy from the evanescent wave exits the opposite end of the crystal and is received by second optical element 1104, which reflects the received light toward ATR detector 1100. ATR detector 1100 receives the reflected light from second optical element 1104. ATR detector 1100 converts the received light into an electrical signal indicating an intensity of the evanescent wave.

In an illustrative embodiment, ATR detector 1100 includes a DLaTGS detector element, a window permitting the light to approach the DLaTGS detector element, and electronics to power the DLaTGS detector element, and to extract the signal information. The window both protects the DLaTGS detector element and is transparent over the desired spectral range. Typically, to perform multi-range IR two detectors are needed: one for the MIR (potassium bromide (KBr) window) and one for the FIR (polyethylene window). In an illustrative embodiment, the window of ATR detector 1100 is a diamond window, which allows a wide spectral range of data collection, from the FIR to the MIR, with one detector, and eliminates the need to swap detectors or insert an additional mirror. Further, the diamond window is not susceptible to moisture damage.

Various components of spectrometer 102 may be operably coupled to processor 118 to receive information from processor 118 and/or to send information to processor 118 under control of control application 114. For example, processor 118 is operably coupled to the light source to control the switching on or off of the one or more light sources. Processor 118 also may be operably coupled to first detector 504, second detector 506, third detector 508, Raman detector 524, and ATR detector 1100 to receive the electrical signals generated by each detector. Processor 118 further may be operably coupled to the referenced actuators to control movement of the various described optical elements and to open and close purge shutters mounted in one or more walls of accessory compartment 300. For example, purge shutters may be mounted to cover second light port 308 and third light port 404 so that an interior of spectrometer 102 can be purged as understood by a person of skill in the art. Processor 118 further may be operably coupled to interferometer 538, validation wheel 546, and/or aperture device 528 to control their operation.

Figure 13:
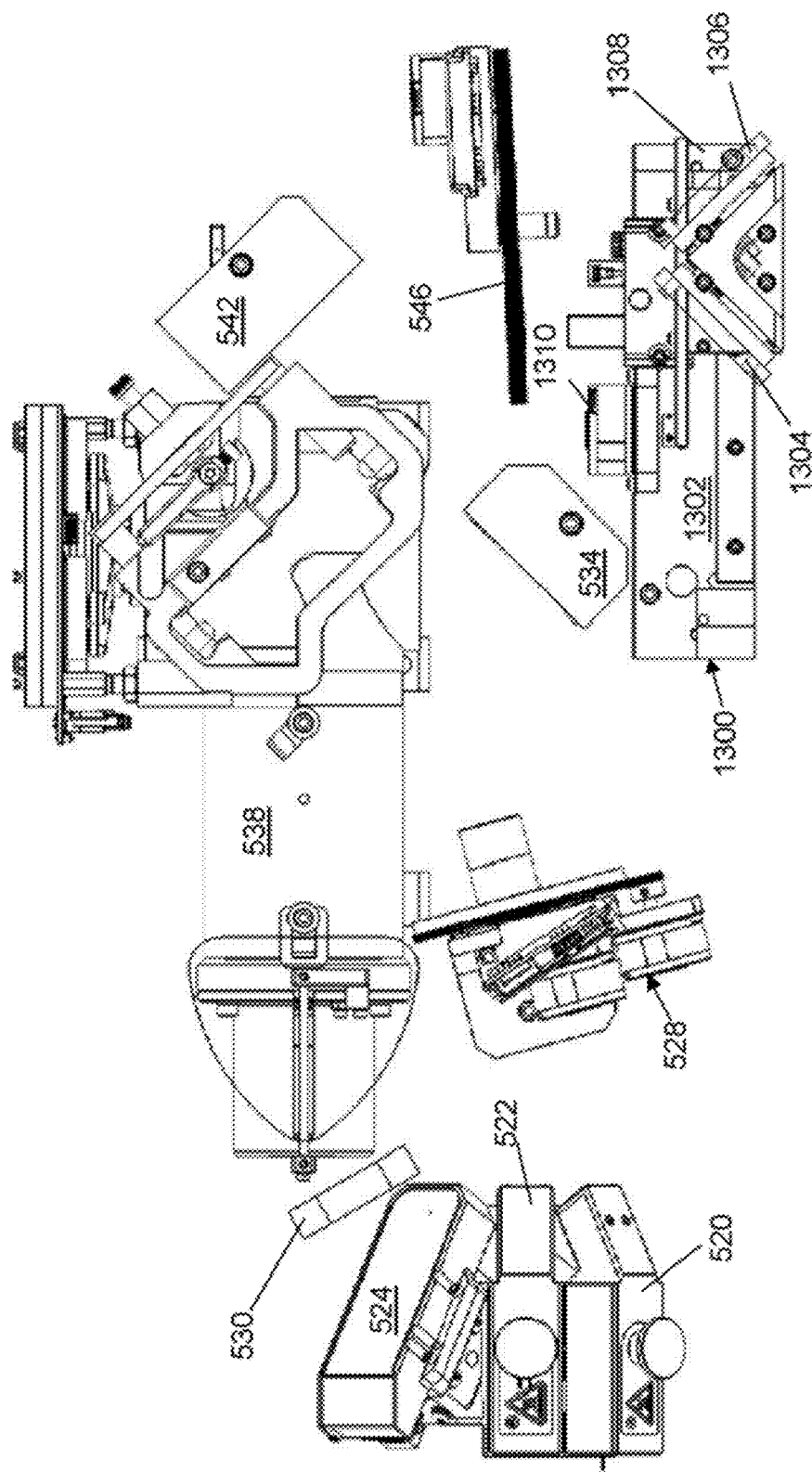
FIG. 13 depicts a top view of a portion of the bench compartment of the spectrometer of FIG. 2 in accordance with a second illustrative embodiment.

With reference to FIG. 13, a top view of components of the bench compartment of spectrometer 102 is shown in accordance with a second illustrative embodiment. In the illustrative embodiment of FIG. 13, spectrometer 102 further includes a first moving mirror device 1300 positioned between optical element 542 and ATR 512 to optionally intercept filtered light 548. First moving mirror device 1300 may include a first plate 1302 mounted to base plate 500, a first optical element 1304 mounted to first plate 1302, a second optical element 1306 mounted to first plate 1302, a first track 1308 formed in first plate 1302, and a first actuator 1310. First optical element 1304 is mounted adjacent second optical element 1306 and at an approximately ninety degree angle with respect to a face of second optical element 1306. Other arrangements may be used depending on the relative orientation of light ports to the exterior of spectrometer 102. First actuator 1310 is mounted to move first optical element 1304 and second optical element 1306 between a first position, a second position, and a third position along first track 1308.

Figure 14:
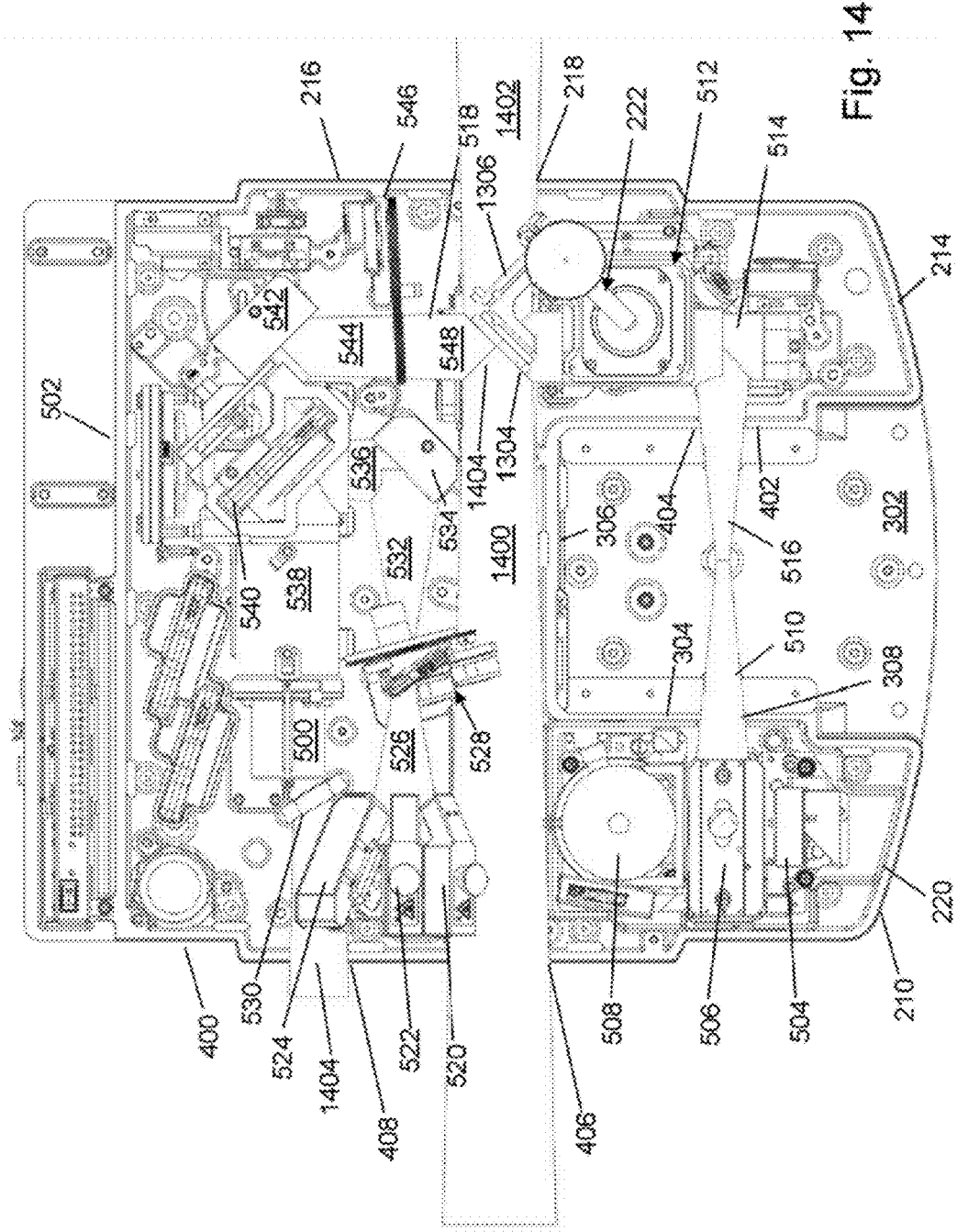
FIG. 14 depicts a top view of the spectrometer of FIG. 13 without any cover plates.

With reference to FIG. 14, a top view of components of the bench compartment of spectrometer 102 is shown in accordance with the second illustrative embodiment. At the first position, as shown in FIG. 14, first optical element 1304 is configured to intercept filtered light 548 from optical element 542 and to reflect light 1400 toward fourth light port 406 to direct light 1400 exterior of spectrometer 102 as defined by base plate 500. At the second position, second optical element 1304 is configured to intercept filtered light 548 from optical element 542 and to reflect light 1402 toward first light port 218 to direct light 1402 exterior of spectrometer 102 as defined by base plate 500. In the second position, a face of second optical element 1304 aligns with a line 1404 as indicated in FIG. 14. At the third position (not shown), neither first optical element 1304 nor second optical element 1306 intercepts filtered light 548 from optical element 542 to allow filtered light 548 to continue toward optical element 514. As further shown in FIG. 14, optical element 530 is positioned to receive light 1404 through fifth light port 408 or to reflect light 1404 through fifth light port 408.

Figure 15:
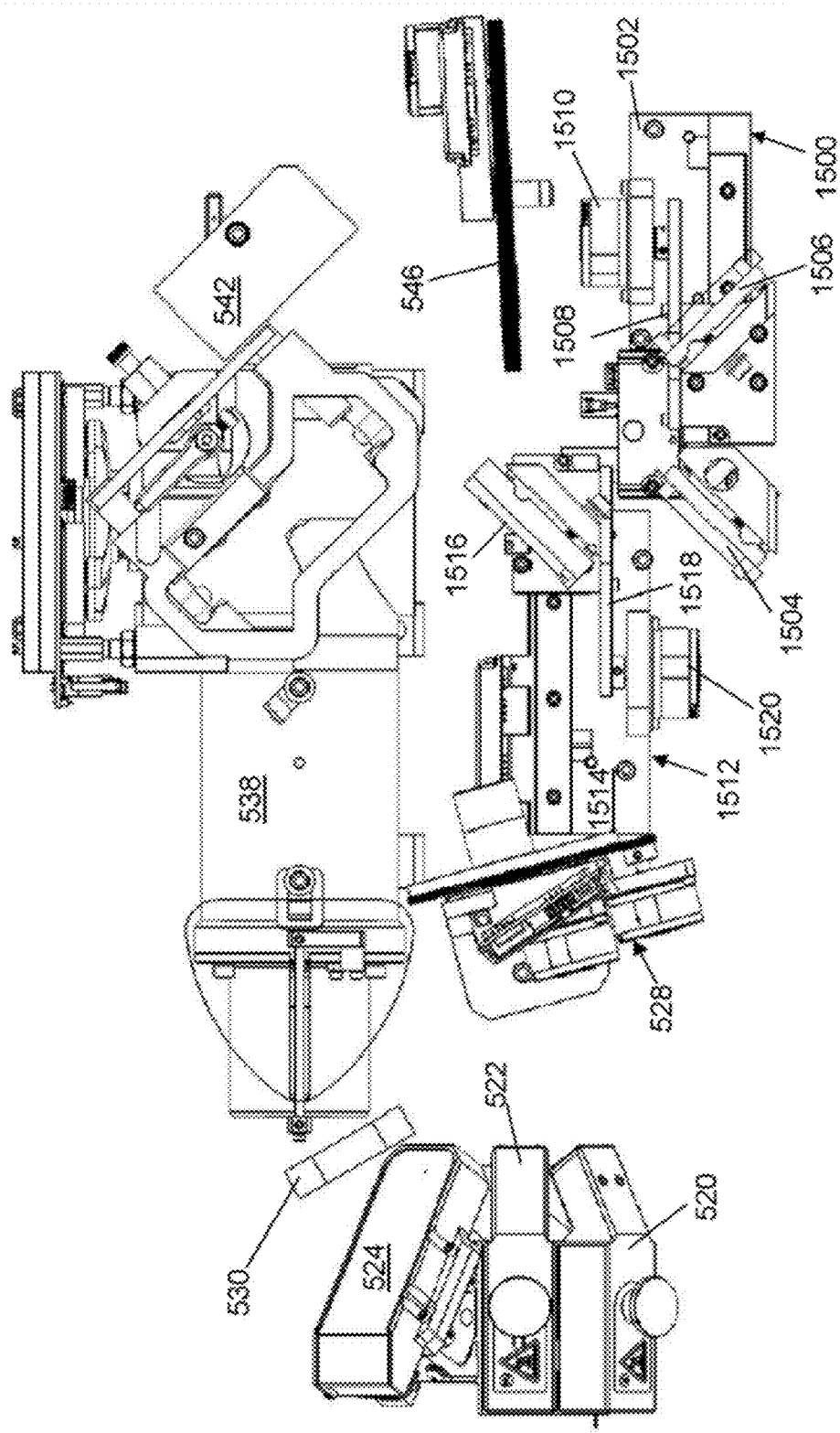
FIG. 15 depicts a top view of a portion of the bench compartment of the spectrometer of FIG. 2 in accordance with a third illustrative embodiment.
Figure 16:
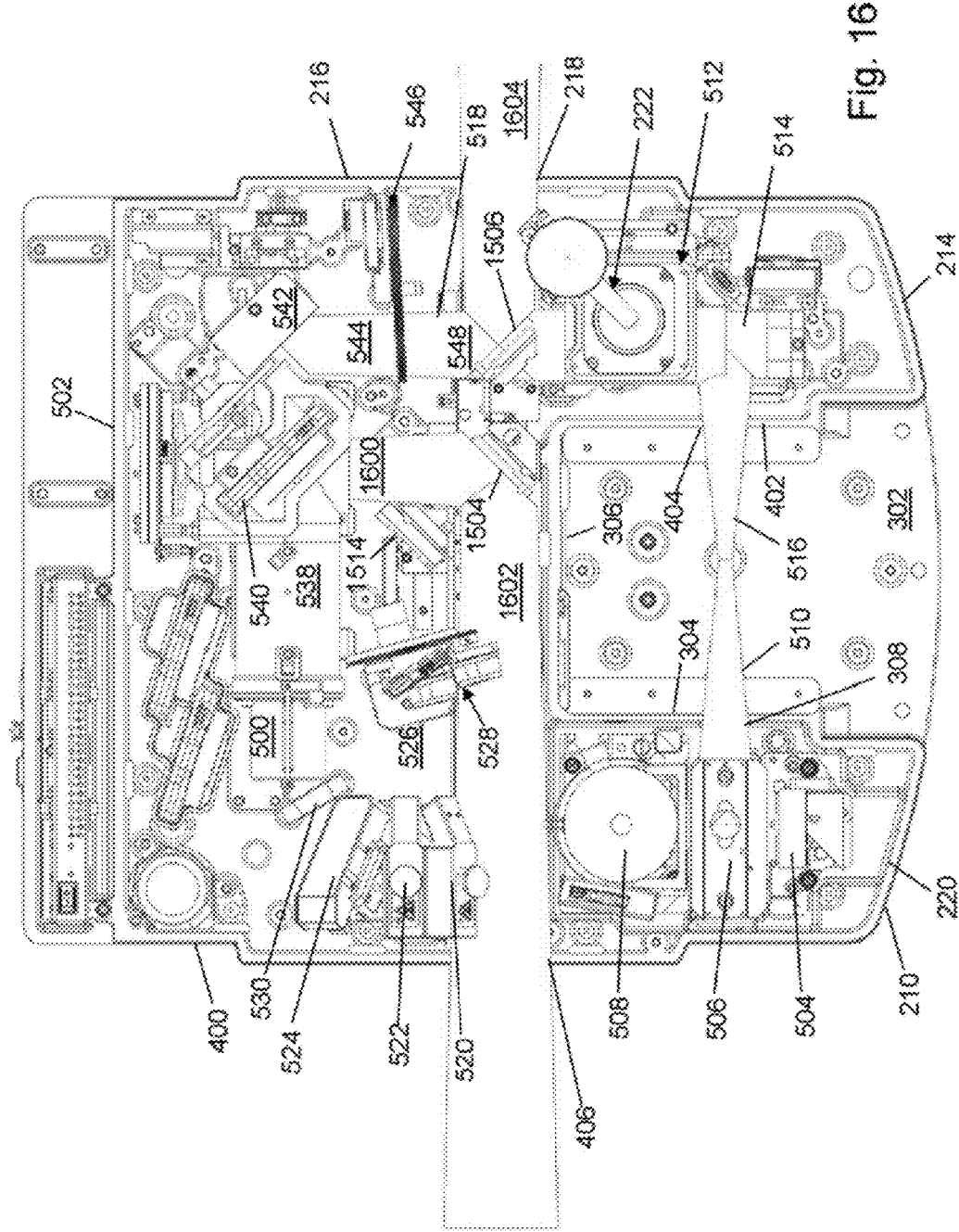
FIG. 16 depicts a top view of the spectrometer of FIG. 15 without any cover plates.

With reference to FIG. 15, a top view of components of the bench compartment of spectrometer 102 is shown in accordance with a third illustrative embodiment. In the illustrative embodiment of FIG. 15, spectrometer 102 further includes a second moving mirror device 1500 and a third moving mirror device 1512. Second moving mirror device 1500 is positioned between optical element 542 and ATR 512 to optionally intercept filtered light 548. Third moving mirror device 1512 is positioned to replace optical element 534 between aperture device 528 and interferometer 538.

Second moving mirror device 1500 may include a second plate 1502 mounted to base plate 500, a fourth optical element 1506 mounted to first plate 1502, a second track 1508 formed in second plate 1502, and a second actuator 1510. A third optical element 1504 is mounted to base plate 500. Third optical element 1504 is mounted at an approximately ninety degree angle with respect to a face of fourth optical element 1506 though again other arrangements are possible depending on the orientation of light ports exterior to spectrometer 102. Second actuator 1510 is mounted to move fourth optical element 1506 between a first position and a second position along second track 1508. Third moving mirror device 1512 may include a third plate 1514 mounted to base plate 500, a fifth optical element 1516 mounted to third plate 114, a third track 1518 formed in third plate 1514, and a third actuator 1520.

With reference to FIG. 17, a top view of components of the bench compartment of spectrometer 102 is shown in accordance with the third illustrative embodiment. Third optical element 1504 is fixed to base plate 500 and is positioned to receive light 1600 from interferometer 538 and to reflect light 1602 toward fourth light port 406 to direct light 1602 exterior of spectrometer 102 as defined by base plate 500. At the first position, fourth optical element 1506 is configured to intercept filtered light 548 from optical element 542 and to reflect light 1604 toward first light port 218 to direct light 1604 exterior of spectrometer 102 as defined by base plate 500. At the second position, fourth optical element 1506 does not intercept filtered light 548 from optical element 542 to allow filtered light 548 to continue toward optical element 514.

Third actuator 1520 is mounted to move fifth optical element 1516 between a first position and a second position along third track 1518. At the first position, fifth optical element 1516 is configured to receive light 532 from aperture device 528 and to reflect light 536 toward interferometer 538 as described previously with reference to optical element 534. At the second position, fifth optical element 1516 does not intercept light 536 from aperture device 528 and is positioned to unblock third optical element 1504 from receiving light 1600 from interferometer 538.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A spectrometer comprising:
   a base plate;
   a light source mounted to the base plate and configured to transmit light;
   an interferometer mounted to the base plate, the interferometer receiving light from the light source and outputting modulated light;
   an accessory compartment configured to accept a sample analysis accessory device, the accessory compartment comprising
      a first wall extending from the base plate, the first wall comprising a first light port configured to accept first light;
      a second wall extending from the base plate; and
      a third wall extending from the base plate between the first wall and the second wall;
   a sample analysis device mounted to the base plate and separated from the accessory compartment by the first wall, the sample analysis device configured to perform attenuated total reflectance analysis of a sample and comprising
      a crystal configured to receive second light;
      a tip configured to press the sample against the crystal; and
      a detector configured to detect third light after reflection of the second light within the crystal;
   a first optical element mounted to the base plate and configured to receive and to reflect the modulated light toward the first light port to form the first light;
   a second optical element mounted to the base plate; and
   an actuator mounted to the second optical element and configured to move the second optical element between a first position and a second position, wherein, in the first position, the second optical element is configured to receive the modulated light and to reflect the modulated light toward the crystal to form the second light such that the first optical element does not receive the modulated light, and further wherein, in the second position, the second optical element does not receive the modulated light.

2. The spectrometer of claim 1, wherein the second wall comprises a second light port configured to accept fourth light formed from the accepted first light.

3. The spectrometer of claim 2, further comprising:
   a plurality of detectors;
   a third optical element configured to receive the fourth light accepted through the second light port; and
   a second actuator mounted to the base plate and configured to move the third optical element between a plurality of positions, wherein at each position of the plurality of positions the third optical element is configured to reflect the received fourth light toward a detector of the plurality of detectors.

4. The spectrometer of claim 1, wherein the detector comprises a detector element and a diamond window, wherein the diamond window is positioned to allow the detector element to receive the third light after passage through the diamond window.

5. The spectrometer of claim 1, wherein the sample analysis device further comprises a third optical element configured to receive the modulated light from the second optical element and to further reflect the modulated light toward the crystal.

6. The spectrometer of claim 5, wherein the sample analysis device further comprises a fourth optical element configured to receive the modulated light from the third optical element and to further reflect the modulated light toward the crystal.

7. The spectrometer of claim 6, wherein the sample analysis device further comprises a fifth optical element configured to receive the third light after reflection within the crystal and to further reflect the third light toward the detector.

8. The spectrometer of claim 7, wherein the third optical element is a parabolic mirror, the fourth optical element is a first elliptical mirror, and the fifth optical element is a second elliptical mirror.

9. The spectrometer of claim 1, wherein the first optical element is a parabolic mirror and the second optical element is a flat mirror.

10. The spectrometer of claim 1, wherein the first wall further comprises a purge shutter plate mounted to the first wall and a second actuator mounted to the purge shutter plate and configured to move the purge shutter plate between a first position and a second position, wherein, in the first position, the purge shutter plate is configured to block the first light port from accepting the first light and to close off the accessory compartment from the sample analysis device, and further wherein, in the second position, the purge shutter plate is configured to unblock the first light port.

11. The spectrometer of claim 1, wherein the light source comprises a first light source configured to emit first light approximately centered at a first wavelength in the visible light spectrum, and a second light source configured to emit second light approximately centered at a second wavelength in the infrared light spectrum.

12. The spectrometer of claim 1, further comprising a third optical element mounted to the base plate and configured to receive the modulated light from the interferometer and to further reflect the modulated light toward the first optical element.

13. The spectrometer of claim 12, further comprising:
a first spectrometer wall extending from the base plate;
a first emission port mounted in the first spectrometer wall;
a plate mounted to the base plate;
a fourth optical element mounted to the plate; and
a second actuator mounted to the fourth optical element and configured to move the fourth optical element between a first position and a second position, wherein, at the first position, the fourth optical element is configured to intercept the modulated light from the third optical element and to reflect the intercepted light toward the first emission port to direct the intercepted light exterior of the spectrometer as defined by the base plate, wherein, at the second position, the fourth optical element does not intercept the modulated light from the third optical element.

14. The spectrometer of claim 13, further comprising:
a fifth optical element mounted to the base plate; and
an aperture mounted to the base plate and configured to receive light from the light source and to transmit the received light toward the fifth optical element;
wherein the fifth optical element is configured to receive light from the aperture and to reflect the received light toward the interferometer.

15. The spectrometer of claim 13, further comprising:
a second spectrometer wall extending from the base plate;
a second emission port mounted in the second spectrometer wall; and
a fifth optical element mounted to the plate, the fifth optical element mounted adjacent the fourth optical element and at an approximately ninety degree angle with respect to a face of the fourth optical element;
wherein the second actuator is further mounted to the fifth optical element and configured to move the fifth optical element between a first position and a second position, wherein, at the first position, the fifth optical element is configured to intercept the modulated light from the third optical element and to reflect the intercepted light toward the second emission port to direct the intercepted light exterior of the spectrometer as defined by the base plate, wherein, at the second position, the fifth optical element does not intercept the modulated light from the third optical element.

16. The spectrometer of claim 15, further comprising:
a sixth optical element mounted to the base plate; and
an aperture mounted to the base plate and configured to receive light from the light source and to transmit the received light toward the sixth optical element;
wherein the sixth optical element is configured to receive light from the aperture and to reflect the received light toward the interferometer.

17. The spectrometer of claim 16, further comprising:
a seventh optical element mounted to the base plate; and
an eighth optical element mounted to the base plate and configured to receive light from the aperture and to reflect the received light toward the seventh optical element;
wherein the seventh optical element is configured to receive the light from the eighth optical element and to reflect the received light exterior of the spectrometer as defined by the base plate.

18. The spectrometer of claim 16, further comprising:
a seventh optical element mounted to the base plate and configured to receive light from exterior of the spectrometer as defined by the base plate; and
an eighth optical element mounted to the base plate;
wherein the seventh optical element is further configured to reflect the received exterior light toward the eighth optical element and the eighth optical element is configured to receive light from the seventh optical element and to reflect the received light toward the aperture.

19. The spectrometer of claim 13, further comprising:
a second spectrometer wall extending from the base plate;
a second emission port mounted in the second spectrometer wall; and
a fifth optical element mounted to the base plate, the fifth optical element mounted at an approximately ninety degree angle with respect to a face of the fourth optical element;
wherein the fifth optical element is configured to receive input light through the second emission port and from exterior of the spectrometer as defined by the base plate and to reflect the received input light toward the interferometer.

20. The spectrometer of claim 19, further comprising:
a second plate mounted to the base plate;
a sixth optical element mounted to the second plate;
an aperture mounted to the base plate and configured to receive light from the light source and to transmit the received light toward the sixth optical element; and
a third actuator mounted to the sixth optical element and configured to move the sixth optical element between a first position and a second position, wherein, at the first position, the sixth optical element is positioned between the fifth optical element and the interferometer and is configured to receive light from the aperture and to reflect the received light toward the interferometer, and further wherein, at the second position, the sixth optical element is not positioned between the fifth optical element and the interferometer.

* * * * *